United States Patent [19]

Driggers et al.

[11] Patent Number: 5,041,287
[45] Date of Patent: Aug. 20, 1991

[54] SPRAYABLE COMPOSITING USING ACETONE SOLVENT

[75] Inventors: Terry L. Driggers, 505 Dance Dr., West Columbia, Tex. 77486; Peter Holemans, Wallingford; W. Novis Smith, Philadelphia, both of Pa.

[73] Assignee: Terry L. Driggers, West Columbia, Tex.

[21] Appl. No.: 479,103

[22] Filed: Feb. 13, 1990

Related U.S. Application Data

[63] Continuation-in-part of Ser. No. 354,825, May 22, 1989, abandoned.

[51] Int. Cl.$^5$ ............................................. A61K 31/78
[52] U.S. Cl. ........................................ 424/81; 424/78; 424/47; 524/568; 524/569
[58] Field of Search ................... 424/78, 81; 604/304; 525/239

[56] References Cited

U.S. PATENT DOCUMENTS 3,339,546  9/1967  Chen ................................ 128/268
4,400,487  8/1983  Stoneberg et al. ................ 525/199
4,786,565  11/1988 Shirai ............................... 428/421

FOREIGN PATENT DOCUMENTS 1317689  5/1973  United Kingdom .

OTHER PUBLICATIONS

Chem. Abstracts, 108; 58034d, Mar. 87.
Chem. Ab. 84:75312w Goda et al., 1976.
Chem. Ab. 85:64330v 3/71.
Chem. Ab. vol. 83, Entry, 33467t, 1972.

Primary Examiner—Thurman K. Page
Assistant Examiner—Peter F. Kulkosky
Attorney, Agent, or Firm—John Lezdey

[57] ABSTRACT

A composition for forming a coating comprising polyvinylidene difluoride and an aqueous emulsion of acrylates, methacrylates, an unsaturated carboxylic acid and/or acrylamide and a solvent having a low boiling point. The composition can be used to form a bandage or glove in situ.

19 Claims, No Drawings

SPRAYABLE COMPOSITING USING ACETONE SOLVENT

This application is a continuation-in-part of application Ser. No. 354,825, filed May 22, 1989, now abandoned.

FIELD OF THE INVENTION

The present invention relates to novel quick coating compositions for providing spray-on bandages for mammals and spray-on gloves and coatings for parts. More particularly, the present invention is concerned with novel flexible bandages or coatings for use on mammals and to provide man with gloves that can be prepared in situ.

DESCRIPTION OF THE PRIOR ART

It is known to provide spray-on bandages not only for human wounds but for use in the field of veterinary medicine. Wounds on the skin of animals require coverings that will not be removed by the animal and which can be easily applied. It is further known to administer a medicament or a local anesthetic or analgesic to both animals and humans which can be delivered over a prolonged period by means of a patch.

U.S. Pat. No. 3,557,516 to Gould et al discloses a spray-on bandage comprised of acrylates, methacrylates and acrylamides for use on humans and for veterinary use. However, the bandage formed does not provide good adhesion or flexibility.

Gloves which are utilized in the health care field should be close fitting, provide good sensitivity and should not be notch sensitive, that is they should be non-tear propagating. Prior to the present invention, the gloves utilized have all been preformed. The disadvantages of preformed gloves is the inability to conform to all hand sizes. Also, the gloves which are now commercially available tend to promote propagation of tearing since they are stretched into a tight fit.

Spray-on bandages and gloves which are formed in situ offer the advantages of providing customized coatings to an area immediately. It is also possible to provide a coating thickness or a glove thickness which is required for a particular situation and which can quickly cover a required area. The requirements for a spray-on bandage include the following:

1. It should protect the wound from air borne bacteria and dirt.
2. It is non-toxic and non-irritating.
3. It should not be water soluble or rendered tacky when in contact with water so as to avoid dirt accumulation.
4. It should be readily removable when desired.
5. It should not adhere to wound area or permit infiltration by regenerating tissue.

It is further desirable to have transparent coatings for parts which can be easily applied or removed. In the case of medical parts it is desirable that the coatings maintain sterility so that the part can be utilized immediately without sterilization. It is further advantageous if the coating itself was able to sterilize the part.

SUMMARY OF THE INVENTION

The present invention relates to a novel coating composition which can provide a rapidly drying coating for use on mammals or as protection for parts.

In accordance with one embodiment of the invention, there is provided a coating composition which can rapidly form a transparent coating over parts such as medical devices and/or electronic components. The coating composition which is formed with some of the solvents and/or additives of the invention results in a sterile contamination-free coating.

In accordance with another embodiment of the invention, there is provided a coating composition which can be sprayed-on or otherwise applied to the human body to provide a protective coating against bacteria or chemical agents. The coating is especially useful on patients to prevent decubitus. The coating can be used as a protective barrier and/or to administer topical medicaments.

The spray-on coating composition containing sterilizing agents such as iodophors can be utilized to coat parts, for example, medical devices and instruments to maintain sterility of the parts prior to use. While acetone is effective to sterilize on contact, the presence of a sterilizing agent such as an iodophor results in extended sterilization even when a tear may occur.

According to another embodiment of the present invention, there is provided a smooth coating composition for forming a coating on a mammal which can be utilized as a protective bandage or to form a glove in situ.

The compositions of the invention comprises about 50 to 90% by weight of polymer solids selected from the group consisting of polyvinylidene difluoride and/or the copolymers thereof, about 10 to 45% by weight of polymer solids of a member selected from the group consisting of a lower alkyl acrylate, a lower alkyl methacrylate, a hydroxy lower alkyl acrylate, an alpha, beta-unsaturated carboxylic acid having an acid number of about 20 to 150, acrylamido, N-lower acrylamide and the copolymers thereof, and a solvent having a low boiling point, preferably less than about 80° C., which can completely dissolve the components.

A preferred composition for forming a non-toxic flexible non-notching coating on a mammal; comprises:

(a) about 50 to 90% by weight of solids of a polymer selected from the group consisting of polyvinylidene difluoride and the copolymers thereof.
(b) about 10 to 45% by weight of polymer solids of an alpha, beta-unsaturated carboxylic acid having an acid number of about 20 to 150, and
(c) a polymer selected from the group consisting of lower alkylacrylate, a lower alkyl methacrylate, acrylamide, an N-lower alkyl acrylamide and the copolymers thereof, and a low boiling solvent in a sufficient amount to practically and rapidly form a coating on a mammal.

It is a feature of the invention that the spray-on composition may be utilized to provide a protective coating on incontinent patients or to simultaneously coat and provide a delivery system to treat and prevent decubitus.

Preferably the composition includes water. More preferably, the composition is prepared by mixing acetone and the polyvinylidene difluoride and/or the copolymers thereof, with an aqueous emulsion of the acrylic compounds. A solution/emulsion having a solids content of about 10 to 30% by weight has been found to be suitable for most coatings. Greater dilution would result in thinner coatings or gloves which can be built up in thickness by repeated application. A greater solids content results in a thicker coating which may require heat for curing.

The coatings of the present invention can also be utilized as vehicles for medicaments which are either intended to treat a skin area on contact or to penetrate and diffuse gradually into the body. The coatings can act as a delivery system or carrier for antiflammatory agents, steroids, iodophors, or the like which are soluble in the solvent.

Physiologically active substances which can be applied with the coatings of the invention include antibiotics, antianemics, anticoagulants, antiphlogistics, disinfectants, chemotherapeutics, hemostatics, cytostatics, hormones and other preparations for external and internal use.

The coating composition of the invention has further applicability to the in situ preparation of gloves for use in the health care industry. The gloves can be formed by dipping the hands into the dispersion or by spraying the dispersion on the hands, or the like. The low boiling solvent which can be used is preferably acetone, which quickly evaporates to leave a tight flexible glove. The glove is not sensitive to notching and has more tactile sensitivity than the preformed gloves. In addition, further layers may be applied as required. The resulting glove is strippable and can be used over a coating which prevents adhesion to the skin.

The composition of the invention can be formed utilizing a polyvinylidene difluoride homopolymer or a copolymer thereof. However, the amount of the copolymer utilized should no be an amount which will effect the characteristics of the polyvinylidene difluoride. Up to about 15% of a copolymer such as polyethylene, methymethacrylate or an acrylate have been found suitable for use in the invention.

Useful lower alkyl acrylates and methacrylates comprise those having 1 to 8 carbon atoms in the alkyl group such as methyl acrylate, ethyl acrylate, isopropyl acrylate, methyl methacrylate, propyl methacrylate, ethoxyethyl acrylate, methoxyethyl acrylate, methoxyethyl methacrylate, ethoxyethyl methacrylate, acrylamide, methacrylamide, N-alkyl substituted acrylamides and methacrylamides such as N-methyl methacrylamide and N-isopropyl methacrylamide and N-vinyl pyrrolidone. Also polymers of the alkyl acrylates and methacrylates with 30-50% hydroxyethyl and hydroxy propyl acrylates and methacrylates are included in this category.

In addition to the acrylic monomer and acrylic monomer mixtures set forth above to prepare polymers there can be added to the monomer or monomer mixture up to about 15% by weight of the total composition acrylic monomers of acrylic acid, methacrylic acid, itaconic acid, maleic acid and fumaric acid.

Preferred alkyl acrylates which can be used to prepared the acrylic polymer dispersant are ethyl acrylate, propyl acrylate, isopropyl acrylate, butyl acrylate, tertiary butyl acrylate, pentyl acrylate, hexyl acrylate, octyl acrylate, nonyl acrylate, decyl acrylate, lauryl acrylate and the like.

To prepare the composition of the invention it is advantageous to prepare an aqueous emulsion of the acrylic compounds prior to admixture with the polyvinylidene difluoride.

One particular useful and preferred aqueous acrylic composition in which dispersions of the acrylic polymer dispersant are used contains the following film-forming constituents:

An acrylic polymer of styrene or methyl methacrylate or a mixture of styrene and methyl methacrylate, a hydroxyalkyl acrylate or a hydroxyalkyl methacrylate and an unsaturated carboxylic acid such as acrylic acid or methacrylic acid in which the polymer had an acid number of about 20–150.

Other preferred acrylic polymer dispersant include the following:
1. methyl methacrylate, butyl acrylate and acrylic acid
2. isodecyl methacrylate, butyl acrylate and acrylic acid
3. stearyl methacrylate, butyl acrylate and acrylic acid
4. methyl methacrylate, 2-ethylhexyl acrylate and methacrylic acid.

Another preferred acrylic polymer dispersant which gives high quality dispersion is of styrene, methyl methacrylate, butyl acrylate and acrylic acid.

A preferred coating for forming a veterinary bandage comprises about 75 to 90% by weight of polyvinyldine difluoride, and 10 to 25% by weight of a mixture of methyl methacrylate, methyl methacrylate copolymer, methyl acrylate and acrylic acid.

It may be desirable to neutralize the acrylic dispersion so as to make it more compatible for use on the skin or to incorporate a medicament.

Typical basic compounds that can be used to neutralize the acrylic polymer dispersant or to adjust the pH of an aqueous dispersion of the polymer dispersant to a pH of about 7 are as follows: ammonium hydroxide, amines, such as primary amines, secondary amines, hydroxyl amines, typical of these amines are diethylethanolamine, ethanolamine, diethanolamine, triethanolamine, N-methylethanolamine, N-aminoethanolamine, N-methyldiethanolamine, monoisopropanolamine, diisopropanolamine, triisopropanolamine, hydroxyalkylamine, butanolamine, hexanolamine, methyldiethanolamine, N.N-dioctylaminoethylamine, ethylenediamine, diethylenetriamine, triethylamine, and the like.

The solvent utilized in the invention are those solvents or a mixture of solvents having a low boiling point, preferably less than 80° C. which completely dissolves the components and quickly evaporates to form a coating. It is essential to achieve complete dissolution to obtain a glove which will not possess notch sensitivity.

Typical solvents that can be used in the dispersion/solution process are diacetone alcohol, acetone, acetylacetone, cyclohexanone, ethylene glycol monoethylether, ethylene glycol monobutyl ether, ethylene glycol monomethylether acetate, tetrahydrofuran and the like. Solvents of limited water solubility can also be used such as methylethyl ketone, pentanone, tetrahydrofuran, ethylene glycol dimethyl ether, and the like.

Most preferable of the solvents is acetone since it is an excellent solvent and acts as a disinfectant.

It is a feature of the invention that the compositions of the invention can be applied utilizing conventional means such as dipping, spraying, coating, etc. For convenience in veterinary treatment and to form a coating or a bandage, the composition can be placed into aerosol form.

Suitable propellants for use in the aerosols include those well known in the art. There can be used compressed gases such as dimethyl ether, carbon dioxide, nitrous oxide, nitrogen, liquified volatile hydrocarbons such as propane, N-butane, isobutane and 2-methylbutane, methylene chloride, vinyl chloride, fluorinated hydrocarbons such as dichlorodifluoromethane (Freon 12), trichlorofluoromethane, 1, 2-1, 1-diluoroethane, vinyl fluoride, vinylidene fluoride, 1-chloro 1, 1 difluoroethane. The propellant should contain a substantial amount of volatile material boiling at not over 20 degrees Celsius, but there can also e present a significant amount of less volatile material boiling up to 50 degrees Celsius.

Platicizers useful for film formation in combination with the polymer-powders include water soluble polar compounds including glycols such as propylene glycol, ethylene glycol, trimethylene glycol, 1, 3, butanediol, 1, 4, butanediol, 2, 5-hexanediol, diethylene glycol, triethylene glycol, tetraethylene glycols and other polyethylene glycols and their methyl and ethyl ethers having a molecular wight up to 800 (e.g. hydroxy terminated polymers of ethylene or polypropylene oxide having average molecular weights of 200–800), dipropylene glycol, tripropylene glycol and other polypropylene glycols having molecular weights up to 900, propylene glycol monoethyl either, di(hydroxypropyl) oxalate, hydroxypropyl acetate, glyceryl tributyrate, liquid sorbitol ethylene oxide adducts, liquid glycerine ethylene oxide adducts, diethylene glycol monomethyl ether, diethylene glycol monoethyl ether, ethylene glycol diacetate.

The amount of plasticizer utilized depends upon the acrylic polymers utilized and the characteristics of the coating desired. About 5 to 10% by weight of plasticizer to solids content has been found suitable for most bandages or gloves.

In practice, it has been found that a light application of the plasticizer to the skin followed by application of the polymer dispersion results in adherence of a sufficient quantity of the power to the area wet with the plasticizer to result in a strong, tough, adherent film. The film can be built up to any desired thickness but is usually about 0.5–1.0 mils.

The following example illustrated the invention. The parts and percentages and ratios are on a weight basis unless otherwise specified.

EXAMPLE 1

A composition suitable for forming gloves or a coating was prepared as follows:

|  | WEIGHT |
| --- | --- |
| Kynar | 24 g. |
| Aqueous acrylic polymer composition | 3 g. |

An aqueous composition containing 35% polymer solids in which the polymer solids are methyl methacrylate/butyl acrylate/hydroxyethyl acrylate/acrylic acid in a weight of about 20,000 determined by gel permeation chromatography using polystyrene as a standard and having 80% of the carboxyl groups neutralized with diethylethanolamine and deionized water.

|  | WEIGHT |
| --- | --- |
| Plasticizer | 1 g. |
| Acetone | 80 g. |

The ingredients were mixed and heated to a temperature of 50° C. The mixture form a gel upon cooling which reversed by reheating.

EXAMPLE 2

A. A neutralized acrylic dispersant is prepared as follows:

|  | PARTS BY WEIGHT |
| --- | --- |
| Aqueous Acrylic polymer Composition of Example 1 | 100 g. |
| Diethanol amine | 22 g. |
|  | 122 g. |

B. A bandage composition was prepared as follows:

| Polyvinylidene difluoride | 22 g. |
| --- | --- |
| Polyvinylidene methyl Methacrylate copolymer | 2 g. |
| Dispersant from part A | 3 g. |
| Acetone | 80 g. |

The mixture was heated to 50° C. to place the ingredients into solution and an additional 80 grams of acetone was added.

5 grams of Lidocaine was added to provide a dispersant for preparing a skin bandage having an anaesthetic effect.

In place of acetone there may be utilized tetrahydrofuran or cyclohexanone.

EXAMPLE 3

A series of experiments were run utilizing commercially available compositions. There was utilized Kynar, a polyvinylidene difluoride power available from Pennwalt, Philadelphia, Pa. Rhoplex B-15, an acrylic polymer having a glass transition temperature of 0° C., a powder available from Rohm & Haas, Philadelphia, Pa., Acryloid A-11, a 30–40% solution of methyl methacrylate and acrylates having a glass transition temperature of 100° C., and acryloid B-44 or methyl methacrylate copolymer having a glass transition temperature of 60° C., each available from Rohm & Haas.

All were mixed together with 80 grams of acetone and heated to 50° C.

| RUN | KYNAR | ACRYLOID A-11 | PHOPLEX B-15 | ACRYLOID B-44 |
| --- | --- | --- | --- | --- |
| A | 24 |  | 3 | 1 |
| B | 24 | 1 | 3 |  |
| C | 25 |  | 2 | 1 |
| D | 23 |  | 4 | 1 |

All of the composition yielded a coating which was tough, resilient, notch resistant and flexible.

EXAMPLE 4

Following the procedure of Example 2 a sprayable dispersion is prepared however, in lieu of Lidocaine, an iodophor is utilized. The resulting composition produces a spray on bandage which releases an effective amount of iodine to treat a wound on a mammal.

What is claimed is:

1. A sprayable composition for forming a smooth non-toxic flexible, non-notching polymeric coating on humans and animals which comprises:

(a) about 50 to 90% by weight of solids selected from the group consisting of polyvinylidene difluoride and the copolymers thereof, (b) about 10 to 45% by weight of solids of a polymer of monomers selected from the group consisting of a lower alkylacrylate, a lower alkyl methacrylate, a hydroxy lower alkylacrylate, a hydroxy lower alkylacrylate, an alpha beta unsaturated carboxylic acid having an acid number of about 20 to 150, acrylamide, an N-lower alkyl acrylamide and the copolymers thereof, and acetone in a sufficient amount to completely dissolve all components and to practically and rapidly form a coating upon evaporation of said acetone at ambient temperatures.

2. The composition of claim 1 including water.

3. The composition of claim 1 comprising about 75 to 90% by weight of polyvinylidene difluoride and 10 to 25% by weight of polymers of methyl methacrylate, methyl methacrylate copolymer, methacrylate and acrylic acid.

4. The composition of claim 3 including a polyvinylidene difluoride copolymer.

5. The composition of claim 1 including a plasticizer.

6. The composition of claim 1 comprising about 10 to 30% by weight solids.

7. The composition of claim 1 in aerosol form.

8. The composition of claim 1 including a medicament.

9. The composition of claim 1 wherein said solvent is a disinfectant.

10. A glove formed in situ on a human from the composition of claim 1.

11. A glove formed in situ on a human from claim 2.

12. A coating formed on a mammal from the composition of claim 1.

13. A coating formed on a mammal from the composition of claim 2.

14. A coating formed on a mammal from the composition of claim 7.

15. A sprayable composition for forming a non-toxic flexible non-notching coating on a mammal comprises:

(a) about 50 to 90% by weight of solids of a polymer selected from the group consisting of polyvinylidene difluoride and the copolymers thereof (b) about 10 to 45% by weight of polymer solids of an alpha, beta unsaturated carboxylic acid having an acid number of about 20 to 150, and (c) a polymer from a monomer selected from the group consisting of lower alkylacrylate, a lower alkyl methacrylate, acrylamide, an N-lower alkyl acrylamide and the copolymers thereof, and acetone in a sufficient amount to completely dissolve all components and and to practically and rapidly form a coating on a mammal upon evaporation of said acetone at ambient temperatures.

16. A process for preparing a sprayable composition which can be used to provide a non-toxic non-notching polymeric coating on the skin of a mammal in situ comprising heating about 50 to 90% by weight of solids of a member selected from the group consisting of polyvinylidene difluoride and the copolymers thereof, and an aqueous dispersion of about 10 to 45% by weight of solids of a polymer of monomers selected from the group consisting of a lower alkylacrylate, a lower alkyl methacrylate, an alpha beta unsaturated carboxylic having an acid number of about 20 to 150, acrylamide, N-lower alkyl acrylamide and the copolymers thereof, with acetone in a sufficient amount to practically and rapidly form a coating in situ on said mammal at ambient temperatures.

17. The process of claim 16, wherein said mixture is heated to a temperature about 50° C.

18. The process of claim 16 including a plasticizing agent.

19. The process of claim 16 wherein said composition comprises about 10 to 30% by weight of polymer solids.

* * * * *